US00PP29591P2

(12) United States Plant Patent
Hansen

(10) Patent No.: US PP29,591 P2
(45) Date of Patent: Aug. 14, 2018

(54) ***DIANTHUS* PLANT NAMED 'ELECTRIC RED'**

(50) Latin Name: ***Dianthus* hybrid**
Varietal Denomination: Electric Red

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/731,783

(22) Filed: Jul. 31, 2017

(51) Int. Cl.
*A01H 5/02* (2018.01)

(52) U.S. Cl.
USPC ..... Plt./278

(58) Field of Classification Search
USPC ..... Plt./278, 283
CPC ..... A01H 5/0233
See application file for complete search history.

*Primary Examiner* — Kent L Bell

(57) ABSTRACT

A new and unique plant cultivar of perennial carnation or pinks, *Dianthus* plant named 'Electric Red' with numerous, medium-sized, semi-double petals of deep red without barring or markings. Compact plant produces highly-glaucous, silvery-colored, linear foliage with vigorous compact habit. *Dianthus* 'Electric Red' is tolerant of high temperatures and resists center die-out.

1 Drawing Sheet

Botanical denomination: *Dianthus* hybrid.
Cultivar designation: 'Electric Red'.

BACKGROUND OF THE INVENTION

The present invention relates to the new and distinct cultivar of carnation or pinks from the genus *Dianthus* and given the cultivar name 'Electric Red'. The new plant was the result of an intentional cross on Jun. 26, 2013 by the inventor between the unreleased proprietary hybrid assigned the breeder code 11-167-01 (not patented) as the female or seed parent and the unreleased proprietary hybrid assigned the breeder code 11-283-1 (not patented) as the male or pollen parent. Seeds of the cross were harvested in the summer of 2013. The new hybrid was first isolated from trials at a wholesale perennial nursery in Zeeland, Mich. during the summer of 2014 as a single seedling and given the breeder number 13-50-1 during the remaining evaluation processes. *Dianthus* 'Electric Red' has been asexually propagated at the same nursery in Zeeland, Mich. since 2014 using traditional shoot tip cutting procedures and found to reproduce plants that are identical and exhibit all the characteristics of the original plant.

No plants of *Dianthus* 'Electric Red' have been sold in this country, or anywhere in the world, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Direct comparison of the new plant with the female parent and male parent are not possible as those plants were not maintained. Comparing the new plant with *Dianthus* 'Red Beauty' U.S. Plant Pat. No. 20,301, the comparison plant is smaller in habit and flower size with only five to seven petals per flower. Compared with the new plant, 'Red Dwarf' U.S. Plant Pat. No. 14,437 has two-tone red petals. The grandparents of the new plant include: 'Devon Xera' U.S. Plant Pat. No. 14,895, 'Pomegranate Kiss' U.S. Plant Pat. No. 21,895 and 'Devon Flavia' U.S. Plant Pat. No. 15,903. Compared with the new plant averaging twenty-seven petals, 'Devon Xera' has five petals, and 'Devon Flavia' has 15 to 20 petals per flower. 'Devon Xera' is taller in flower than the new plant and the flowers petals of 'Devon Xera' have a darker purple-red band while the flower petals of the new plant are lacking the darker band.

*Dianthus* 'Electric Red' is distinct from its parents and all other *Dianthus* known to the applicant in the following combined traits:

1. semi-double flowers of vibrant, rich deep, red petals.
2. Petals having moderately serrated apex.
3. Plants producing many flower stems with excellent flower coverage over the entire mound in mid-spring with over 600 flowers on two-year old plants.
4. Floriferous, vigorous, with compact habit and finely-textured silvery-colored foliage.

BRIEF DESCRIPTION OF THE DRAWINGS

The photographs of *Dianthus* 'Electric Red' demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
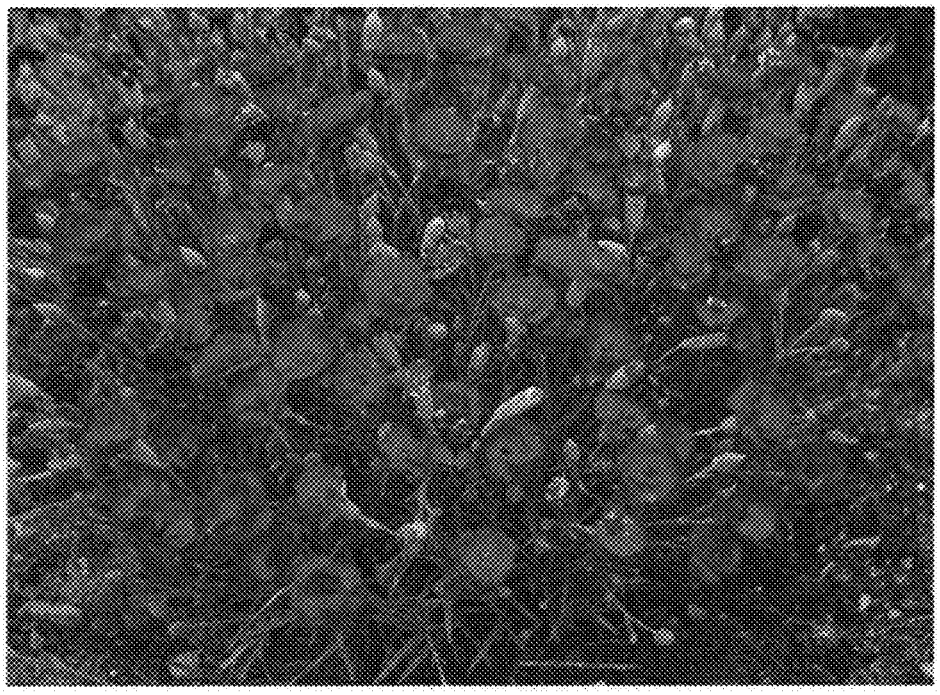
FIG. 1 shows the habit of a two-year-old plant in mid-season flowering.
Figure 2:
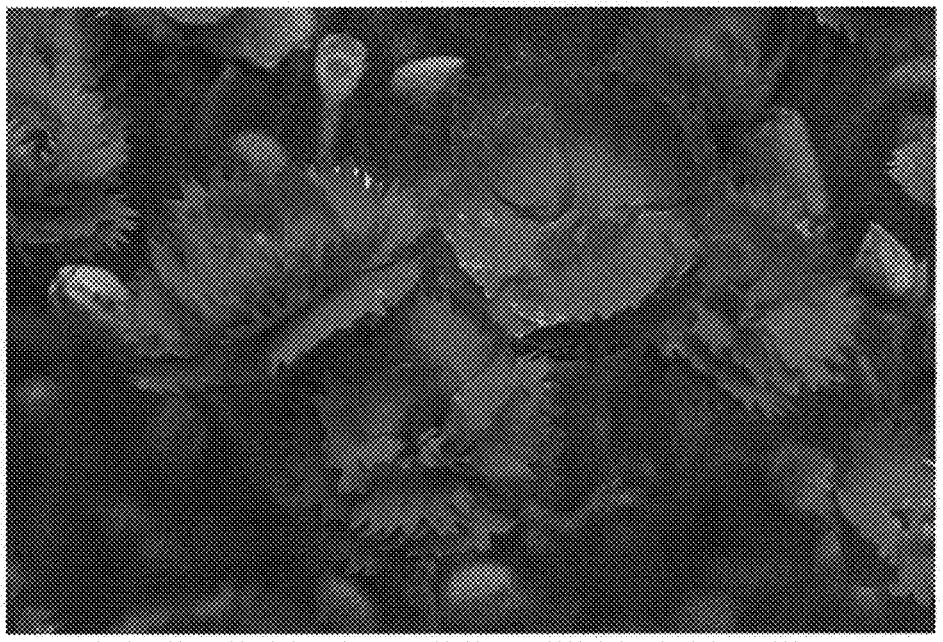
FIG. 2 shows a close-up of the flowers and early buds.

The following detailed description of the new plant is based on observations of two-year old plants in greenhouse-grown containers at a nursery in Zeeland, Mich. with light shade, supplemental watering, light additions of fertilizer and free of other plant growth regulators. All color usage is in accordance with the 2001 edition of The Royal Horticultural Colour Chart except where common dictionary terms are used.

Botanical classification: *Dianthus* hybrid;

Parentage: Proprietary unreleased hybrid 11-167-1 as the female or seed parent ('Fire Star' x 'Pomegranate Kiss'), and proprietary unreleased hybrid 11-283-1 as the male or pollen parent ('Candy Floss' x 'Pomegranate Kiss');

Plant description:

*Habit*.—Caespitose, herbaceous, evergreen perennial; stems and peduncles branched, erect to arching with weight, number and size of flowers; height of foliage about 16.0 cm and about 46.0 cm across; size in flower is about 23.0 cm tall and 68 cm wide.

*Root system*.—Fine, fibrous; color nearest RHS 155D.

*Vigor*.—Good; spring-planted vernalized plugs finish in 3.8 liter pots in seven to eight weeks.

Foliage:

*Leaf type*.—Simple, linear, opposite, decussate; glabrous, glaucous on adaxial and abaxial; acute apex; base sessile, decurrent, adpressed along stem; no fragrance detected.

*Leaf dimensions*.—Average about 3.3 cm long and about 3.5 mm wide.

*Leaf color*.—Young expanding leaves abaxial and adaxial nearest RHS 145A proximally and RHS 138B distally; mature adaxial between RHS 122A and RHS N138D, abaxial between RHS N138C and RHS 122A.

*Venation*.—Not pronounced; obscurely pinnate, coloration same as that of leaf top and bottom.

Stems: Beginning erect and becoming slightly arching with development of flowers; terete, glabrous, glaucous, branching at alternate distal nodes; about 130 per plant;

*Stem size*.—About 18.0 cm long and about 4.0 mm wide at base.

*Stem color*.—Nearest RHS N138C.

*Branching*.—Numerous, alternate from lower leaf axils; about 8 per main stem; branch size average about 3.5 cm long at time of initial flowering.

*Nodes*.—Typically 8 to 10 per stem; about 3.5 mm across; color nearest RHS 157D.

*Internodes*.—Average about 1.2 cm apart depending on growing temperature and position on stem, shorter in cooler conditions and at base.

Inflorescence:

*Type*.—Terminal, cymose; salverform; actinomophic; semi-double.

*Attitude*.—Upright to slightly arching.

*Dimension*.—About 4.6 cm across and extending about 36.0 mm above calyx tube base.

*Flowers per stem*.—Two to three.

*Pedicel*.—Glaucous, glabrous, terete.

*Pedicel size*.—Terminal flower average about 1.9 cm long and about 2.0 mm diameter; other flowers average about 14.0 mm long and 1.5 mm diameter.

*Pedicel color*.—Nearest RHS 188A.

*Flower bud one day prior to opening*.—Glaucous, glabrous, ellipsoidal with rounded apex and rounded base; style not exserted at bud stage.

*Flower bud size*.—One day prior to opening — about 2.3 cm long and about 9.0 mm wide; while petals still enclosed in calyx — about 16.0 mm long and about 7.0 mm wide.

*Flower bud color*.—While still enclosed in calyx — between RHS 139C and RHS 139D at apex and between RHS 145D and RHS 139D at base; with petals exposed and still tight — petals between RHS 59A and RHS 59B and calyx same as while petals still enclosed in calyx.

*Flower period*.—Beginning mid to late spring; effective about four to five weeks per flowering season.

*Flower fragrance*.—Not detected.

*Flower lasting quality*.—About seven days on or cut from plant.

*Petals*.—Glabrous; 24 to 32 per flower, average 27; consisting of a rounded blade or limb and a claw, outer petals with broader and more rounded limb; limb obovate with long tapered claw apex with medium dentations 2.0 mm deep; limb bent outwardly in distal 12.0 mm to nearly a ninety degree angle; persistent.

*Petal color*.—Petal claw abaxial and adaxial base between RHS 145D and RHS 145C, distally lighter than RHS 59D; abaxial main limb nearest RHS 60A; adaxial main limb nearest RHS 60A; without dark bar or other markings.

*Petal dimension*.—To about 32.0 mm long and 21.0 mm across at widest part of limb, average about 30.0 mm long and about 15.0 mm wide; claw portion average about 16.0 mm long and about 1.0 mm at base; limb portion average about 14.0 mm long and 18.0 mm wide.

*Calyx*.—Glabrous, glaucous; forming five-toothed corolla tube about 1.7 cm long and about 7.0 mm across.

*Sepals*.—Glaucous, glabrous; margins entire; apex acute, fused in basal 14.0 mm; 17.0 cm long.

*Calyx color*.—Abaxial nearest RHS 138B with veins of nearest RHS; adaxial nearest RHS 145A.

*Peduncle*.—Glabrous, glaucous, terete, average about 13.5 cm long and about 2.0 mm diameter at base.

*Peduncle color*.—Nearest RHS 189B.

*Bracts*.—Two sets; both opposite, glaucous, glabrous, with sessile bases and margin entire; inner set broadly obtuse to deltoid with acute apex, outer set cordate with acuminate apex; outer set about 8.0 mm long and about 7.0 mm wide, inner set about 7.0 mm long and about 5.0 mm wide.

*Bract color*.—Both sets the same; abaxial longitudinal center nearest RHS 135A, margins translucent nearest 157B; adaxial longitudinal center nearest RHS 137A, margins translucent nearest 157B.

*Androecium*.—Absent or up to twelve, typically vestigial; up to 10.0 mm long; Filaments: when present, variable in length from 6.0 mm to 8.0 mm long, less than about 1.0 mm diameter; color nearest RHS 155A; Anther: rare; sagittate to irregular, dorsifixed;

typically not fully formed; about 1.0 mm long and about 0.3 mm wide; color nearest RHS N186A; Pollen: not observed.

*Gynoecium*.—Pistil: typically split in two just above ovary; Style: glabrous abaxial surface and puberulent adaxial surface; curled around about 360 degrees in terminal 3.0 mm; natural length about 14.0 mm and about 1.0 mm diameter at base; color base white, transitioning distally to nearest RHS N79B on adaxial side and lighter than RHS N77C on abaxial side; Stigma: puberulent; about 1.0 cm long and 1.0 mm wide; irregularly curled; color nearest RHS 72D; Ovary: superior; ellipsoid-shaped; about 8.0 mm long and 3.5 mm wide; color nearest RHS 145B distally and between RHS 145C and RHS 145D proximally.

Fruit: Capsule; ovoid to cylindrical; opening by 4 teeth; about 0.6 cm long and 4.5 mm diameter; color between RHS 164C and RHS 164D when dried;

Seed: Not observed;

Disease resistant: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct *Dianthus* plant named 'Electric Red' essentially as herein described and illustrated.

* * * * *